United States Patent
Whitsitt et al.

(10) Patent No.: US 10,692,592 B2
(45) Date of Patent: Jun. 23, 2020

(54) SYNCHRONIZATION OF HEALTHCARE DATA ACROSS DISPARATE DATA CENTERS

(71) Applicant: Cerner Innovation, Inc., Kansas City, KS (US)

(72) Inventors: Greg Whitsitt, Lee's Summit, MO (US); Micah Whitacre, Olathe, KS (US); Andrew Olson, Kansas City, MO (US)

(73) Assignee: Cerner Innovation, Inc., Kansas City, KS (US)

( * ) Notice: Subject to any disclaimer, the term of this patent is extended or adjusted under 35 U.S.C. 154(b) by 756 days.

(21) Appl. No.: 14/258,338

(22) Filed: Apr. 22, 2014

(65) Prior Publication Data

US 2015/0302147 A1 Oct. 22, 2015

(51) Int. Cl.
*G16H 10/60* (2018.01)
*G06F 19/00* (2018.01)

(52) U.S. Cl.
CPC ............. *G16H 10/60* (2018.01); *G06F 19/00* (2013.01)

(58) Field of Classification Search
CPC ................ G06Q 50/22–24; G06F 19/322–327
See application file for complete search history.

(56) References Cited

U.S. PATENT DOCUMENTS

| | | | |
|---|---|---|---|
| 2002/0032583 A1* | 3/2002 | Joao | G06F 19/322 705/2 |
| 2005/0071194 A1* | 3/2005 | Bormann | G06F 17/30578 705/2 |
| 2007/0061393 A1 | 3/2007 | Moore | |
| 2007/0162306 A1 | 7/2007 | Peters | |
| 2013/0304506 A1 | 11/2013 | Gallivan et al. | |
| 2014/0275835 A1* | 9/2014 | Lamego | A61B 5/14551 600/301 |

OTHER PUBLICATIONS

First Action Interview Pilot Program Pre-Interview Communication dated Feb. 12, 2016 in U.S. Appl. No. 14/812,689, 4 pages.
(Continued)

*Primary Examiner* — Robert A Sorey
(74) *Attorney, Agent, or Firm* — Shook, Hardy & Bacon L.L.P.

(57) ABSTRACT

Methods, systems, and computer-readable media are provided for synchronizing healthcare data across disparate data centers. Healthcare data from healthcare data sources is received by a collector service that operates in a cloud computing platform. The data is sent to a staging platform associated with a first data center that is hosting the collector service. From here, the data is stored in association with a long-term storage data store associated with the first data center. As well, it is communicated to processing nodes associated with the first data center that subscribe to the data. The staging platform also communicates the data to a staging platform associated with a second data center. This staging platform also stores the data in association with a long-term storage data store located at the second data center and communicates the data to processing nodes located at the second data center that subscribe to the data.

20 Claims, 5 Drawing Sheets

(56) References Cited

OTHER PUBLICATIONS

First Action Interview Pilot Program Pre-Interview Communication dated Feb. 12, 2016 in U.S. Appl. No. 14/707,627, 4 pages.
First Action Interview Office Action dated Jun. 20, 2016 in U.S. Appl. No. 14/707,627, 5 pages.
First Action Interview Office Action dated Jun. 21, 2016 in U.S. Appl. No. 14/812,689, 5 pages.
Final Office Action dated Jul. 11, 2018 in U.S. Appl. No. 14/812,689, 17 pages.
Notice of Allowance received for U.S. Appl. No. 14/707,627, dated Mar. 26, 2019, 12 pages.

* cited by examiner

SYNCHRONIZATION OF HEALTHCARE DATA ACROSS DISPARATE DATA CENTERS

BACKGROUND

Computing platforms that ingest and process healthcare data face a number of challenges. For example, there has been a dramatic increase in the number of computer application solutions that utilize healthcare data to generate outcome data that is relevant to clinicians and patients. Locating the processing nodes that execute these solutions close to where the healthcare data is ingested and stored may be unfeasible as the healthcare data sets expand into the petabyte range. Co-locating the processing nodes with the underlying healthcare data may also be unfeasible due to physical size constraints of the data centers that host the nodes and/or rack availability at these data centers. As a result, processing nodes that subscribe to certain sets of healthcare data may not always be located at the data center where the healthcare data is received and stored.

This scenario may create a number of different problems. For example, a computing solution that utilizes a defined set of healthcare data from a healthcare data source may be located at a first data center, and another solution that requires the same set of healthcare data may be located at a second geographically-disparate data center. In this case, a crawler would need to pull the set of healthcare data from the healthcare data source twice, with one upload occurring at the first data center and a second upload occurring at the second data center. This process consumes valuable processing resources and Internet bandwidth at the healthcare data source. It is also duplicative and increases data center hosting costs. In another example, a new computing solution may be deployed at a data center, but the healthcare data needed by this new solution may be located at a different data center. In a typical case, the healthcare data would have to be re-extracted from the data source which once again consumes computing resources at the data source and increases data center hosting costs.

Another challenge faced by healthcare operating platforms is the loss of healthcare data due to, for example, a natural or man-made disaster occurring at the data center hosting the data. Because modern-day medicine relies heavily on the use of computer applications to aid decision making, loss of data hosted at a data center can significantly impair the healthcare delivery process. This problem becomes even more critical when the data that is lost is no longer available from the data's source.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. The present invention is defined by the claims.

In brief, and at a high level, the present invention is directed to methods, systems, and computer-readable media for synchronizing healthcare data across multiple, disparate data centers. Healthcare data sources such as, for example, healthcare organizations upload their data to a data collector service that is part of a cloud computing platform. The data collector service acts as a front door to any number of different data centers. As the data collector service receives the healthcare data it is placed in a staging platform associated with a first data center that is hosting the collector service. The staging platform comprises durable, short-term storage (e.g., a durable cache) which allows for quick access to the healthcare data. Moreover, the data is durably replicated across multiple servers in the staging platform such that the failure or loss of an individual staging platform server does not result in the data being lost. Additionally, the data is indexed such that it is available for low-latency processing.

Once the data is in the staging environment, it is stored in a long-term storage data store associated with the first data center; this data store is optimized for long-term storage of healthcare data. As well, it is determined if any processing nodes at the first data center subscribe to or utilize the received healthcare data when implementing its solutions. If so, the data is communicated to those processing nodes where it is subsequently processed to generate clinically-relevant outcomes.

In addition, the data is communicated to a staging platform associated with a second data center. The staging platform stores the healthcare data in a long-term storage data store associated with the second data center and also may communicate the data to any processing nodes at the second data center that subscribe to the data. Storing the received healthcare data in long-term storage data stores associated with disparate data centers facilitates data recovery in the event that one of the data centers is compromised by, for example, a natural or man-made disaster. Moreover, efficiently delivering the data to those data centers and processing nodes that have expressed an interest in the data eliminates the need to re-crawl the healthcare data source for the needed data.

BRIEF DESCRIPTION OF THE DRAWINGS

Embodiments are described in detail below with reference to the attached drawing figures, wherein.

DETAILED DESCRIPTION

Figure 1:
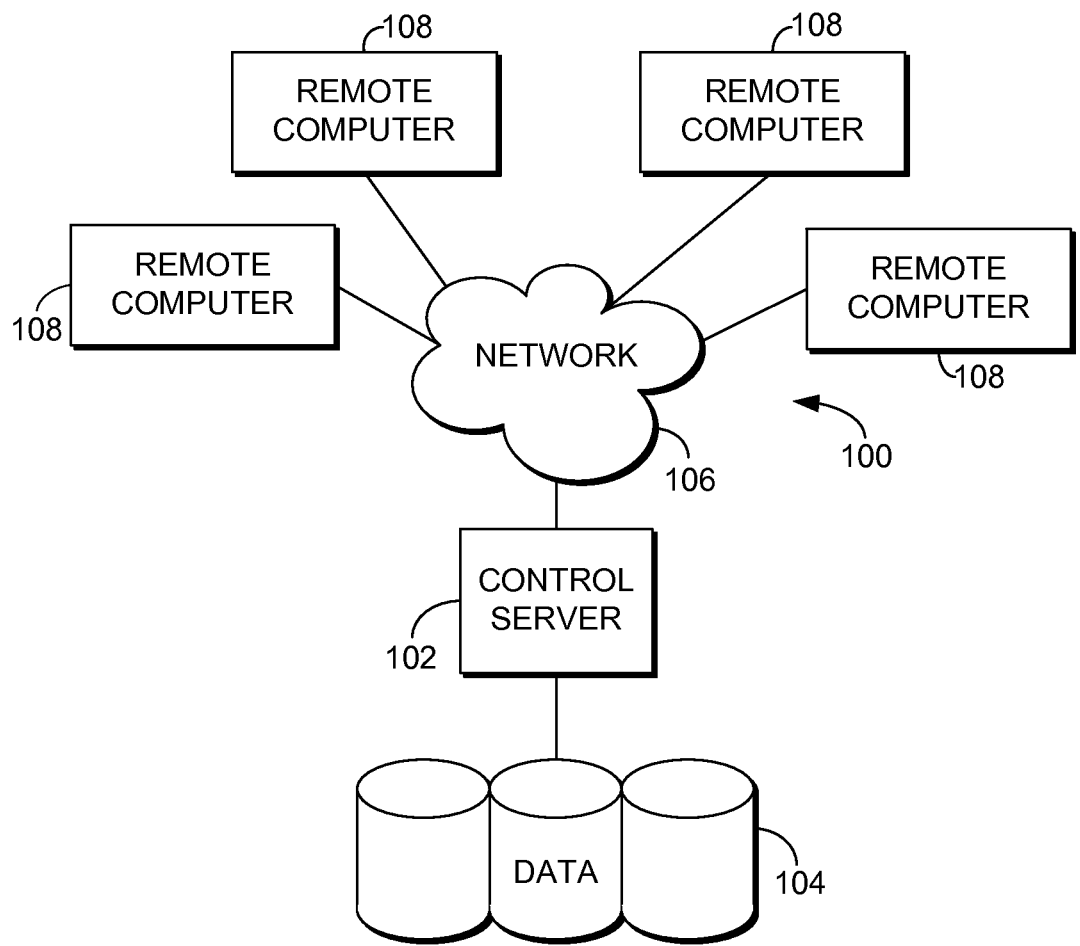
FIG. 1 is a block diagram of an exemplary computing environment suitable to implement embodiments of the present invention.

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

Embodiments of the present invention are directed to methods, systems, and computer-readable media for synchronizing healthcare data across multiple, disparate data centers. A data collector service associated with a cloud computing platform receives healthcare data from one or more healthcare data sources. Once received, the data is sent to a staging platform associated with a first data center. The staging platform stores the healthcare data such that it can be quickly accessed, and it also indexes the data so that is optimized for low-latency (e.g., real-time) processing. The staging platform also stores the healthcare data in a long-term storage data store associated with the first data center. The long-term storage data store is optimized to store the healthcare data for long periods of time, potentially never deleting the data. This is useful in the event that the data is needed at a future point of time (i.e., when implementing a new computing solution) and obviates the need to re-crawl the data's source to obtain the needed data.

Additionally, the staging platform communicates the healthcare data to any processing nodes associated with the first data center that subscribe to or utilize the data. These processing nodes may perform either batch processing or low-latency processing on the data, depending on the nature of the computing solution implemented by the particular node. In the event a processing node is performing batch processing of the data, the staging platform is configured to store the data in the long-term storage data store until it is needed by the node. In the event a processing node is performing low-latency processing on the healthcare data, the staging platform is configured to immediately communicate the received healthcare data to the node.

As well, the staging platform associated with the first data center is configured to communicate the received healthcare data to a staging platform associated with a second data center where it is subsequently stored in a long-term storage data store associated with the second data center. This process ensures that the data is stored in at least two geographically-disparate data centers in the event that the data is corrupted or destroyed at one of the data centers. The staging platform associated with the second data center may further communicate the data to processing nodes associated with the second data center that utilize or subscribe to the healthcare data. Once the healthcare data has been stored in at least two long-term storage data stores associated with disparate data centers, and once the healthcare data has been communicated to all the processing nodes that subscribe to the data regardless of where the processing nodes are physically located, the healthcare data stored by the staging platforms may be removed or deleted so as to free up storage or cache space for new incoming healthcare data.

The cloud computing platform described above not only provides full disaster recovery capabilities, but also effectively moves healthcare data closer to the processing nodes that subscribe to the data—even if those processing nodes are located at geographically-disparate data centers. Additionally, the cloud computing platform described above enables a particular healthcare data source to upload a particular piece of data a single time to the platform as opposed to, for example, having to upload the particular piece of data to each of the data centers that utilize the data. This saves the healthcare data source valuable processing resources and Internet bandwidth, and reduces data center hosting costs.

An exemplary computing environment suitable for use in implementing embodiments of the present invention is described below. FIG. 1 is an exemplary computing environment (e.g., medical-information computing-system environment) with which embodiments of the present invention may be implemented. The computing environment is illustrated and designated generally as reference numeral 100. The computing environment 100 is merely an example of one suitable computing environment and is not intended to suggest any limitation as to the scope of use or functionality of the invention. Neither should the computing environment 100 be interpreted as having any dependency or requirement relating to any single component or combination of components illustrated therein.

The present invention might be operational with numerous other purpose computing system environments or configurations. Examples of well-known computing systems, environments, and/or configurations that might be suitable for use with the present invention include personal computers, server computers, hand-held or laptop devices, multi-processor systems, microprocessor-based systems, set top boxes, programmable consumer electronics, network PCs, minicomputers, mainframe computers, distributed computing environments that include any of the above-mentioned systems or devices, and the like.

The present invention might be described in the general context of computer-executable instructions, such as program modules, being executed by a computer. Exemplary program modules comprise routines, programs, objects, components, and data structures that perform particular tasks or implement particular abstract data types. The present invention might be practiced in distributed computing environments where tasks are performed by remote processing devices that are linked through a communications network. In a distributed computing environment, program modules might be located in association with local and/or remote computer storage media (e.g., memory storage devices).

With continued reference to FIG. 1, the computing environment 100 comprises a computing device in the form of a control server 102. Exemplary components of the control server 102 comprise a processing unit, internal system memory, and a suitable system bus for coupling various system components, including data store 104, with the control server 102. The system bus might be any of several types of bus structures, including a memory bus or memory controller, a peripheral bus, and a local bus, using any of a variety of bus architectures. Exemplary architectures comprise Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

The control server 102 typically includes therein, or has access to, a variety of non-transitory computer-readable media. Computer-readable media can be any available media that might be accessed by control server 102, and includes volatile and nonvolatile media, as well as, removable and nonremovable media. By way of example, and not limitation, computer-readable media may comprise computer storage media and communication media. Computer storage media includes both volatile and nonvolatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by control server 102. Communication media typically embodies computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above should also be included within the scope of computer-readable media.

The control server 102 might operate in a computer network 106 using logical connections to one or more remote computers 108. Remote computers 108 might be located at a variety of locations in a medical or research environment, including clinical laboratories (e.g., molecular diagnostic laboratories), hospitals and other inpatient settings, veterinary environments, ambulatory settings, medical billing and financial offices, hospital administration settings, home healthcare environments, and clinicians' offices. Clinicians may comprise a treating physician or physicians; specialists such as surgeons, radiologists, cardiologists, and oncologists; emergency medical technicians; physicians' assistants; nurse practitioners; nurses; nurses' aides; pharmacists; dieticians; microbiologists; laboratory experts; laboratory technologists; genetic counselors; researchers; veterinarians; students; and the like. The remote computers 108 might also be physically located in nontraditional medical care environments so that the entire healthcare community might be capable of integration on the network. The remote computers 108 might be personal computers, servers, routers, network PCs, peer devices, other common network nodes, or the like and might comprise some or all of the elements described above in relation to the control server 102. The devices can be personal digital assistants or other like devices.

Computer networks 106 comprise local area networks (LANs) and/or wide area networks (WANs). Such networking environments are commonplace in offices, enterprise-wide computer networks, intranets, and the Internet. When utilized in a WAN networking environment, the control server 102 might comprise a modem or other means for establishing communications over the WAN, such as the Internet. In a networking environment, program modules or portions thereof might be stored in association with the control server 102, the data store 104, or any of the remote computers 108. For example, various application programs may reside on the memory associated with any one or more of the remote computers 108. It will be appreciated by those of ordinary skill in the art that the network connections shown are exemplary and other means of establishing a communications link between the computers (e.g., control server 102 and remote computers 108) might be utilized.

In operation, an organization might enter commands and information into the control server 102 or convey the commands and information to the control server 102 via one or more of the remote computers 108 through input devices, such as a keyboard, a microphone (e.g., voice inputs), a touch screen, a pointing device (commonly referred to as a mouse), a trackball, or a touch pad. Other input devices comprise satellite dishes, scanners, or the like. Commands and information might also be sent directly from a remote healthcare device to the control server 102. In addition to a monitor, the control server 102 and/or remote computers 108 might comprise other peripheral output devices, such as speakers and a printer.

Although many other internal components of the control server 102 and the remote computers 108 are not shown, such components and their interconnection are well known. Accordingly, additional details concerning the internal construction of the control server 102 and the remote computers 108 are not further disclosed herein.

Figure 2:
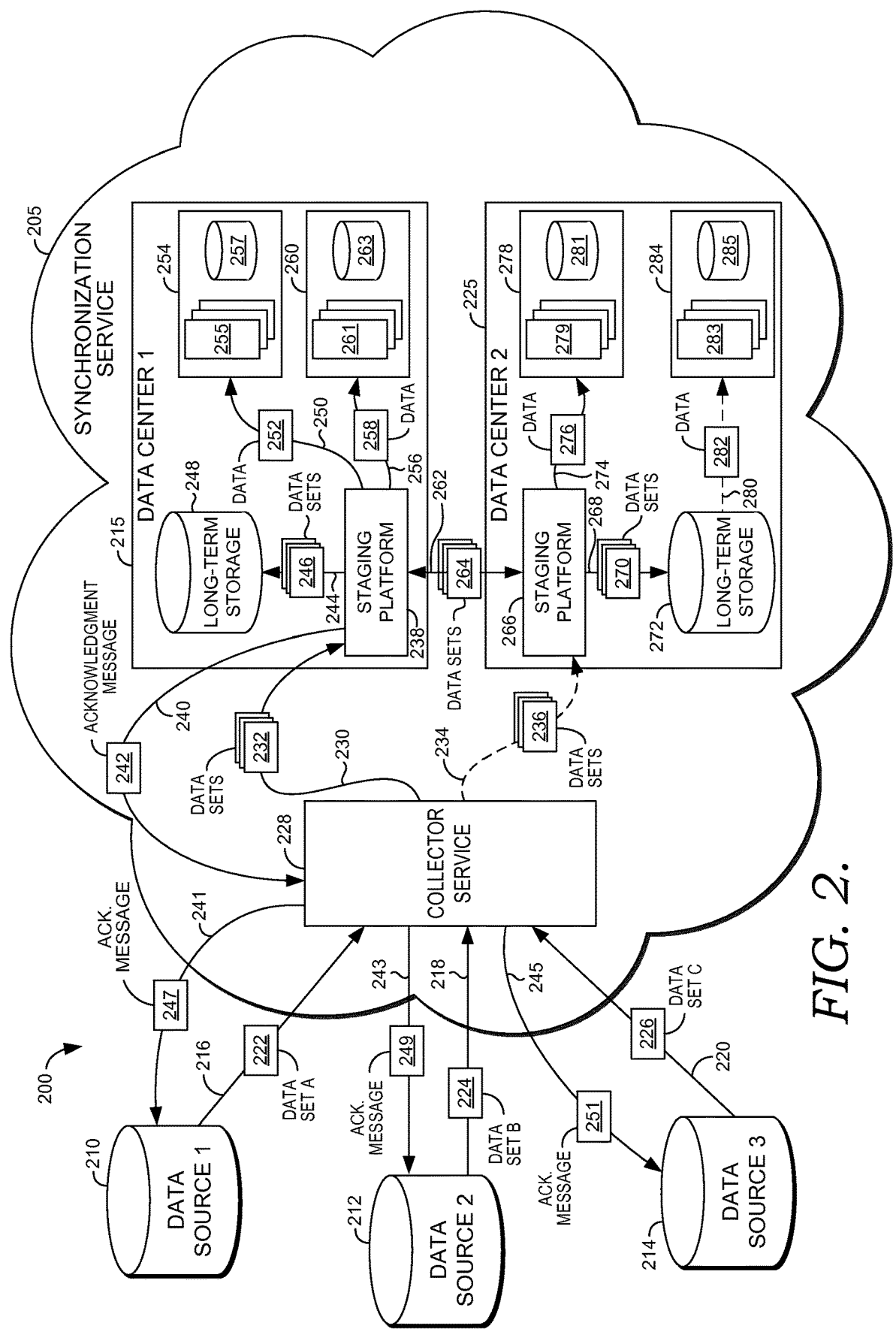
FIG. 2 is a block diagram of an exemplary system for synchronizing healthcare data across multiple, disparate data centers suitable to implement embodiments of the present invention.

Turning now to FIG. 2, a block diagram 200 is illustrated, in accordance with an embodiment of the present invention, showing an exemplary synchronization service 205 implemented in a cloud computing platform. It will be understood and appreciated that the cloud computing platform shown in FIG. 2 is merely an example of one suitable computing system environment and is not intended to suggest any limitation as to the scope of use or functionality of embodiments of the present invention. For instance, the cloud computing platform may be a public cloud, a private cloud, or a dedicated cloud. Neither should the cloud computing platform be interpreted as having any dependency or requirement related to any single component or combination of components illustrated therein. Further, although the various blocks of FIG. 2 are shown with lines for the sake of clarity, in reality, delineating various components is not so clear, and metaphorically, the lines would more accurately be grey and fuzzy. In addition, any number of physical machines (such as computing devices or portion of computing devices 108 shown in FIG. 1), virtual machines, data centers, endpoints, or combinations thereof may be employed to achieve the desired functionality within the scope of embodiments of the present invention. As mentioned, the cloud computing platform comprises a cloud-computing network, which is known in the art as "the cloud."

As shown in FIG. 2, the synchronization service 205 is capable of communicating with a number of different entities or data sources such as the healthcare data sources 210, 212, and 214 for the collection of healthcare data. This communication may utilize, without limitation, one or more local area networks (LANs) and/or wide area networks (WANs). Such networking environments are commonplace in offices, enterprise-wide computer networks, intranets, and the Internet. Accordingly, the network is not further described herein. As used throughout this application, the term "healthcare data" is meant to be broad and encompass any type of healthcare information. The healthcare data may be specific to a single patient or a group of patients. The healthcare data may also be directed to a clinician or group of clinicians. For example, healthcare data as it relates to a clinician may include patients that the clinician treats.

The healthcare data sources 210, 212, and 214 may include, for example, a hospital, a physician's office, a health information exchange, an urgent care clinic, and the like. Healthcare data received from these different sources 210, 212, and 214 may include, but is not limited to, information that describes various aspects of the patient state, including patient vitals, lab results, medication orders, diagnosis codes, condition codes, clinical orders, indexed values from clinical notes or other text documents, patient demographic information, patient history, patient images, and a variety of other patient information.

It should be noted that the healthcare data sources 210, 212, and 214 shown as communicating with the synchronization service 205 in FIG. 2 are provided by way of example only and are not intended to limit the scope of the present invention in any way. Each healthcare data source 210, 212, and 214 may have one or more computing devices such as computing device 108 of FIG. 1, for communicating with the synchronization service 205. Each healthcare data source 210, 212, and 214 may maintain its own native electronic medical record (EMR) system. Further, the healthcare data sources 210, 212, and 214 may be disparate from each other such that the data sources 210, 212, and 214 are not directly connected with one another. In one aspect, the healthcare data sources 210, 212, and 214 send information to the synchronization service 205 and not typically directly between one another.

Further, the healthcare data sources 210, 212, and 214 may be able to access the synchronization service 205 in a variety of ways within the scope of the present invention. For example, in some embodiments, a healthcare data source may have a native clinical computing system, which may be able to communicate with the synchronization service 205. In other embodiments, a client application associated with the synchronization service 205 may reside or partially reside on one or more of the healthcare data sources' computing devices facilitating communication with the synchronization service 205. In further embodiments, communication may simply be a web-based communication, using, for example, a web browser to communicate with the synchronization service 205 via the Internet. Any and all such variations are contemplated to be within the scope of embodiments of the present invention.

As shown in FIG. 2, the synchronization service 205 comprises a collector service 228, a first data center 215, and a second data center 225. The collector service 228 is configured to receive or extract healthcare data from each of the data sources 210, 212, and 214 as either a stream of data and/or in batches. The collector service 228 collects the healthcare data by one of several methods. For instance, the collector service 228 may include, in one aspect, a program that extracts relevant data from the data sources 210, 212, and 214. For example, the collector service 228 may extract relevant healthcare data for a particular patient from the patient's EMR. The healthcare data may include a complete historical record of a patient's EMR along with any updates or modifications to the patient's EMR. Updates are received or extracted by the collector service 228 substantially simultaneously with when the information is updated in the patient's EMR. In another aspect, the collector service 228 may query the data sources 210, 212, and 214 to obtain patient information. In yet another aspect, the healthcare data sources 210, 212, and 214 may utilize a Web interface to upload their data.

The collector service 228 spans multiple data centers such as the data center 215 and the data center 225. In other words, the collector service 228 acts as a "front door" that receives healthcare data from the different sources 210, 212, and 214 without regard to which data center will eventually process the data. From the perspective of the data sources 210, 212, and 214, these data sources simply upload their data to the collector service 228 instead of having to upload their data to each of the data centers (e.g., the data centers 215 and 225) that will eventually process their data. In one exemplary aspect, the collector service 228 may be available to each of the data sources 210, 212, and 214 through a Web interface. Each data source 210, 212, and 214 is provided with a uniform resource locator (URL) (e.g., a URL referencing the collector service 228) by which to upload the healthcare data. Because of the characteristics of the synchronization service 205, which will be explained in greater depth below, a single piece of healthcare data need only be uploaded once to the collector service 228. The piece of healthcare data does not have to be re-uploaded in the event of, for example, physical loss of data at one of the data centers 215 or 225, or the introduction of a new computing solution at one of the data centers 215 or 225 that utilizes the particular piece of data.

As mentioned, the synchronization service 205 further includes the data center 215 and the data center 225. The data centers 215 and 225 are contemplated as being located in geographically-disparate locations. Although only two data centers are depicted in FIG. 2, it is contemplated that the synchronization service 205 may include multiple, geographically-disparate data centers. In general, only one data center hosts the collector service 228 at any given time, although any of the data centers associated with the synchronization service 205 are capable of hosting the collector service 228. As shown in FIG. 2, the data center 215 is currently hosting the collector service 228. What is meant by the term "hosting" will be explained in greater depth below.

Taking the data center 215 as a representative example, the data center 215 comprises at least a staging platform 238, a long-term storage data store 248, a first processing node 254, and a second processing node 260. The components associated with the data center 215 are equally applicable to the data center 225. Further, the descriptions of these various components are equally applicable to both the data center 215 and the data center 225 unless indicated otherwise.

As mentioned, the data center 215 is currently hosting the collector service 228. This means that healthcare data received by the collector service 228 from the data sources 210, 212, and 214 is communicated to the staging platform 238 associated with the data center 215. If the staging platform 238 is not available to receive the healthcare data from the collector service 228, then staging platform 266 associated with the data center 225 may be used to receive the data from the collector service 228.

The staging platform 238 comprises a durable cache that provides quick access to the healthcare data. Once healthcare data has been accepted into the staging platform 238, the data is durably replicated across multiple servers in the staging platform. Thus, the failure or loss of an individual staging platform server does not result in the data being lost. The staging platform 238 indexes the healthcare data in such a way that it is accessible for low-latency processing. As well, healthcare data stored in association with the staging platform 238 is generally categorized by source (e.g., data source 210, 212, or 214).

The staging platform 238 is optimized for several different functions. First, the staging platform 238 is configured to communicate an acknowledgment message to the collector service 228 once it has accepted the healthcare data; the collector service 228, in turn, communicates an acknowledgment message to each of the healthcare data sources 210, 212, and 214 acknowledging receipt of the data. The staging platform 238 is also configured to store the data in association with the long-term storage data store 248. The long-term storage data store 248 is configured to store the data for long periods of time, potentially never deleting the data. Healthcare data stored in the long-term storage data store 248 is generally stored as-is with the addition of metadata describing the data's source and when it was received. Data stored in association with the long-term storage data store 248 can be accessed for use by, for example, analytic workflows that may need to utilize data that was received months or even years ago. As well, data stored in association with the long-term storage data store 248 can also be accessed by new computing solutions implemented by processing nodes within the data center 215 or even by existing computing solutions that did not need the data at the time it was received.

Returning to the staging platform 238, the staging platform 238 is additionally configured to communicate the healthcare data to one or more of the processing nodes 254 and 260. With respect to this aspect, routing logic associated with the synchronization service 205 determines which processing nodes subscribe to or utilize the healthcare data. Based on this determination, the staging platform 238 communicates the healthcare data or subsets of the healthcare data to the appropriate processing node.

Further, the staging platform 238 is adapted to route the healthcare data to staging platforms associated with other data centers, such as the staging platform 266 associated with the data center 225. The determination of which data center(s) to route the healthcare data may be determined by the routing logic discussed above. For example, if it is determined that processing nodes associated with a particular data center(s) subscribe to the healthcare data, then the healthcare data is routed to this particular data center(s). In another example, if it is determined that the only processing nodes that are currently subscribing to the healthcare data are those associated with the data center 215, then the routing logic determines a data center located in a geographically-disparate location to which to communicate the healthcare data (where it is subsequently stored in the center's long-term storage data store to facilitate data recovery in disaster situations). It is contemplated that the staging platform 238 may communicate the healthcare data to multiple disparate data centers depending on whether processing nodes associated with those data centers subscribe to the data.

Once the healthcare data accepted by the staging platform 238 has been stored in association with the long-term storage data store 248, communicated to a staging platform associated with a disparate data center (such as the staging platform 266 associated with the data center 225), and communicated to those processing nodes that subscribe to the healthcare data (either processing nodes associated with the data center 215, processing nodes associated with disparate data centers, or both), the healthcare data may be deleted from the staging platform 238. This helps to ensure that sufficient cache space is available at the staging platform 238 for new incoming healthcare data.

The processing nodes 254 and 260 are each adapted to implement a healthcare solution. In some cases, these may be the same computing solution, and in other cases these may be different computing solutions. Although only two processing nodes are shown in association with the data center 215 and the data center 225, it is contemplated that each data center may comprise more than two processing nodes. Each processing node 254 and 260 includes, for example, a plurality of parallel processors, 255 and 261 respectively, and a storage engine 257 and 263 respectively. The storage engines 257 and 263 are configured to temporarily store the healthcare data utilized by the respective parallel processors 255 and 261. The parallel processors 255 and 261 may be optimized for batch processing and/or low-latency (e.g., real-time) processing depending on the healthcare solution implemented at the particular processing node. By way of illustrative example, the processing node 254 may implement a solution that provides clinicians with up-to-date views of patient data. As such, it performs low-latency processing on a generally continuous stream of healthcare data received, via the staging platform 238, from the data sources 210, 212, and 214. By contrast, the processing node 260 may implement a solution that analyzes outcomes associated with aggregated sets of healthcare data. A solution such as this does not generally require continually-updated information but may, instead, perform batch processing on data received every, for example 24 hours.

As described above, the processing nodes 254 and 260 may receive data from the staging platform 238. For low-latency processing, healthcare data at the staging platform 238 is indexed and immediately sent to the processing node executing the low-latency processing. In the event that a processing node associated with the data center 225 (e.g., the processing nodes 278 and/or 284) performs low-latency processing on the data, the staging platform 266 immediately communicates the needed data to the low-latency processors after it has received the data from the staging platform 238. The result of this is that data received from a data source is immediately available to processing nodes subscribing to the data regardless of whether the processing nodes are located at geographically-disparate data centers.

For batch processing, healthcare data at the staging platform 238 may be communicated to the storage engines associated with the processing nodes 254 and 260 (e.g., the storage engines 257 and/or 263). The storage engines 257 and/or 263 may store the healthcare data until it is needed by the processing node executing the batch processing. In another aspect, data needed for batch processing may be accessed from the long-term storage data store 248. In yet another aspect, the long-term storage data store 248 may be utilized as a storage engine for a particular processing node at the data center 215.

The healthcare data stored in association with the long-term storage data store 248 may also be accessed by the processing nodes 254 and 260 for different reasons. For example, this may occur when an existing data source (e.g., healthcare facility) requests enrollment in a computer solution implemented by one of the processing nodes 254 or 260. Instead of having to re-extract the data needed by this solution from the data source, the processing node 254 or 260 can simply access the data from the long-term storage data store 248. As well, this may occur when a new computing solution is added to the data center 215 that utilizes the healthcare data. Any and all such aspects, and any variation thereof, are contemplated as being within the scope of the invention.

Still with reference to FIG. 2, a process-flow will now be described to better illustrate the claimed invention. At a step 216, the data source 210 communicates a data set A 222 to the collector service 228. Likewise, at a step 218, the data source 212 communicates a data set B 224 to the collector service 228, and at a step 220, the data source 214 communicates a data set C 226 to the collector service 228. In each case, the data sources 210, 212, and 214 may, for example, utilize a URL to upload the data sets 222, 224, and 226 to the collector service 228. The data sets 222, 224, and 226 may comprise historical records of patients' EMRs, and/or they may comprise updates to data already stored in association with the synchronization service 205.

At a step 230, the collector service 228 communicates the data sets 222, 224, and 226 (labeled as data sets 232) to the staging platform 238 associated with the data center 215. The data collected from each of the data sources 210, 212, and 214 is kept separate. Alternatively, and as shown by the dashed arrow, if the data center 225 was hosting the collector service 228, the collector service 228 would, at a step 234, communicate the data sets 222, 224, and 226 (labeled as data sets 236) to the staging platform 266 associated with the data center 225.

Once the staging platform 238 receives the data sets 232 from the collector service 228, it communicates, at a step 240, an acknowledgment message 242 to the collector service 228. The collector service 228, in turn, communicates respectively at steps 241, 243, and 245, acknowledgement messages 247, 249, and 251 to each of the data sources 210, 212, and 214 acknowledging that the data sets 222, 224, and 226 have been accepted into the staging platform 238.

At a step 244, the staging platform 238 stores the data sets (now labeled as data sets 246) in association with the long-term storage data store 248 which persistently stores the data sets 246 to facilitate disaster recovery as well as to obviate the need for re-extraction from the data sources 210, 212, and 214 in the event that data within the data sets 246 is needed at a future point in time.

Based on the processing node 254 subscribing to some or all of the data contained in the data sets 232, the staging platform 238, at a step 250, communicates data 252 to the processing node 254 where it is subsequently processed to generate clinically-relevant information. The processing may be batch processing and/or low-latency processing conditioned on the nature of the computing solution hosted by the processing node 254. Depending on whether the data sources 210, 212, and 214 have enrolled in the solution hosted by the processing node 254, the data 252 may comprise some or all of the data sets communicated by the healthcare data sources 210, 212, and 214 to the synchronization service 205 (e.g., data sets 222, 224, and 226). As well, depending on the nature of the solution implemented by the processing node 254, a particular source's entire data set or a subset of the source's data set may be included in the data 252. Similarly, based on the processing node 260 subscribing to some or all of the data contained in the data sets 232, at a step 256, the staging platform 238 communicates data 258 to the processing node 260 where it is subsequently processed to generate clinically-relevant outcome data. In the event that each of the processing nodes 254 and 260 implements different solutions, the data 258 may differ from the data 252. If the processing nodes 254 and 260 implement the same solution, then the data 258 may be the same as the data 252. The step 250 may occur concurrently with the step 244 (e.g., the staging platform storing the data sets 246 in association with the long-term storage data store 248).

At a step 262, the staging platform 238 communicates the data sets (labeled as data sets 264) to the staging platform 266 associated with the data center 225. The arrow between the data centers 215 and 225 is shown as being bi-directional to indicate that if the data center 225 is hosting the collector service 228, the staging platform 266 would be communicating the data sets 264 to the staging platform 238 associated with the data center 215. The step 262 may occur concurrently with the steps 244, 250, and 256. After the staging platform 238 has completed these actions, the data sets 232 may be deleted from the staging platform 238 to free up cache space.

The determination of which disparate data center to communicate the data sets 264 may be based on, for example, whether processing nodes associated with the disparate data center subscribe to some or all of the data in the data sets 264, or, in the event that no further processing nodes subscribe to the data contained in the data sets 264, the determination may be based on the geographic location of the disparate data center (i.e., to facilitate disaster recovery, a data center located a predetermined distance away from the data center 215 may be selected).

Once accepted into the staging platform 266 of the data center 225, the staging platform 266 stores the data sets 264 in such a way that data within the data sets 264 is easily accessible. Further, it indexes the data in the data sets 264 to make it accessible for low-latency processing. At a step 268, the staging platform 266 stores the data sets (labeled as data sets 270) in association with the long-term storage data store 272 associated with the data center 225. As well, based on the processing node 278 subscribing to some or all of the data in the data sets 264, at a step 274, the staging platform 266 communicates data 276 to the processing node 278 which subsequently processes the data 276 (utilizing batch processing, low-latency processing, or a combination of both) to generate clinically-relevant outcome information. The data 276 may comprise some or all of the data in the original data sets 222, 224, and/or 226 received from the healthcare data sources 210, 212, and 214. The steps 268 and 274 may occur concurrently with each other.

As shown in FIG. 2, the staging platform 266, based on routing logic, does not communicate data to the processing node 284. This may be because the processing node 284 does not subscribe to the type of data contained in the data sets 264, or it may be because the healthcare data sources 210, 212, and 214 are not currently enrolled in the computing solution hosted by the processing node 284. However, if at a later point in time, one or more of the data sources 210, 212, and/or 214 enroll in the solution hosted by the processing node 284, the processing node 284 can access the needed data from the long-term storage data store 272. This is indicated in FIG. 2 by the dashed line 280 illustrating that data 282 is communicated to the processing node 284 from the long-term storage data store 272. Like the staging platform 238, once the staging platform 266 associated with the data center 225 carries out these steps, the healthcare data may be deleted from the staging platform 266.

Although the process-flow shown in FIG. 2 depicts data being communicated between two data centers, it is contemplated that the staging platform 238 associated with the data center 215 may communicate the data to multiple, disparate data centers. This may occur when processing nodes associated with each of the multiple, disparate data centers subscribe to the data accepted into the staging platform 238.

Figure 3:
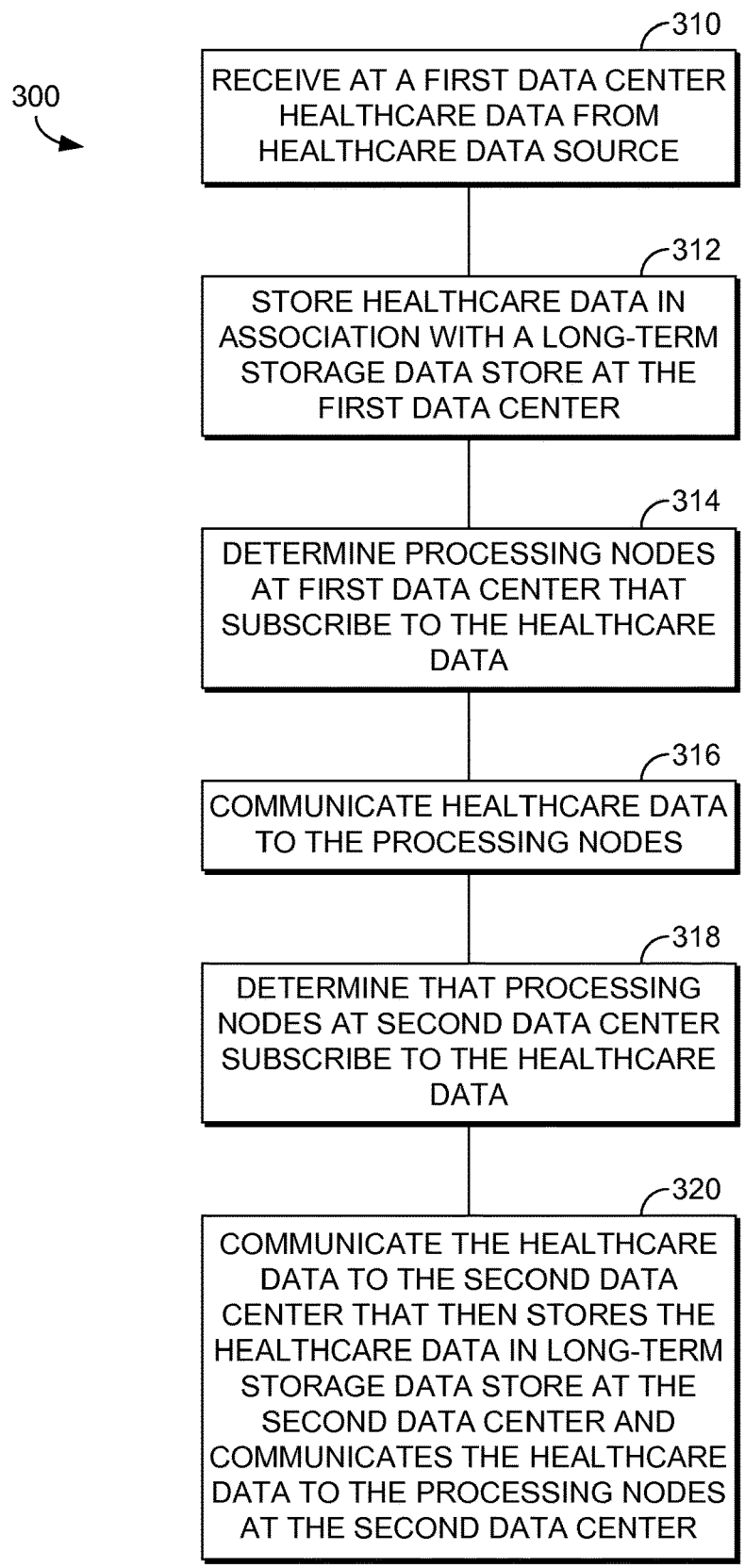
FIGS. 3-5 are flow diagrams of exemplary methods of synchronizing healthcare data across multiple, disparate data centers in accordance with embodiments of the present invention.

Turning now to FIG. 3, a flow diagram is depicted of an exemplary method 300 of synchronizing healthcare data across multiple data centers. Although the term "step" may be used herein to connote different elements of methods employed, the term should not be interpreted as implying any particular order among or between various steps herein disclosed unless and except when the order of individual steps is explicitly described.

The method 300 may be carried out by a synchronization service such as the synchronization service 205 of FIG. 2. At a step 310, healthcare data is received at a first data center from a healthcare data source such as, for example, a healthcare facility. The healthcare data may comprise historical EMR information and/or it may comprise updates to information already stored in association with the synchronization service. The data may be received as a continuous or substantially continuous stream of data, and/or the data may be received in batches. The healthcare data may be initially received by a collector service, such as the collector service 228 of FIG. 2 that acts as a "front door" to the first data center. From the collector service, the data is sent to a staging platform associated with the first data center, such as the staging platform 238 associated with the data center 215 of FIG. 2.

At a step 312, the healthcare data is stored in association with a long-term storage data store associated with the first data center, such as the long-term storage data store 248 of FIG. 2. In the event the healthcare data comprises an update to already-existing information in the long-term storage data store, the updated healthcare data is stored as a new version. The long-term storage data store persistently stores the data and makes it available in the event of, for example, disaster recovery, implementation of a new computing solution, and/or an existing processing node needing the data at a later point in time.

At a step 314, one or more processing nodes associated with the first data center (such as the processing nodes 254 and 260 of FIG. 2) that subscribe to the healthcare data are determined. The determination may be based on routing logic executed by synchronization service. The routing logic, in turn, takes into account the different computing solutions subscribed to by the healthcare data source. At a step 316, the healthcare data is communicated to the processing nodes that have been determined to utilize the data. The processing nodes subsequently process the healthcare data to produce clinically-relevant outcome data that is eventually provided to, via one or more computer applications, clinicians and/or patients.

At a step 318, it is determined that one or more processing nodes associated with a second geographically-disparate data center (such as the data center 225 of FIG. 2) also subscribe to the healthcare data received from the healthcare data source. At a step 320, the healthcare data is communicated to the second data center. The second data center stores the data in association with its long-term storage data store and also communicates the healthcare data to the processing nodes that subscribe to the healthcare data. The processing nodes subsequently process the data using batch processing, low-latency processing, or both to produce clinically-relevant information.

The steps 312, 314, and 318 may be carried out substantially concurrently with each other. In other words, the healthcare data may be stored in the data center's long-term storage data store at substantially the same time as the determination of which processing nodes, both at the first data center and the second data, subscribe to the healthcare data.

The method 300 ensures that the healthcare data source need only upload the healthcare data a single time to the synchronization service. Because the healthcare data is persistently stored in at least two geographically-disparate long-term storage data stores, the healthcare data is available for later use without having to re-extract the data from the healthcare data source. For example, a new computing solution may be implemented at the first (or second) data center. The solution may be implemented in association with one or more processing nodes. Healthcare data needed by this solution can be retrieved from the first (or second) data center's long-term storage data store and processed by the new solution as opposed to having to re-extract the data from the healthcare data source.

Figure 4:
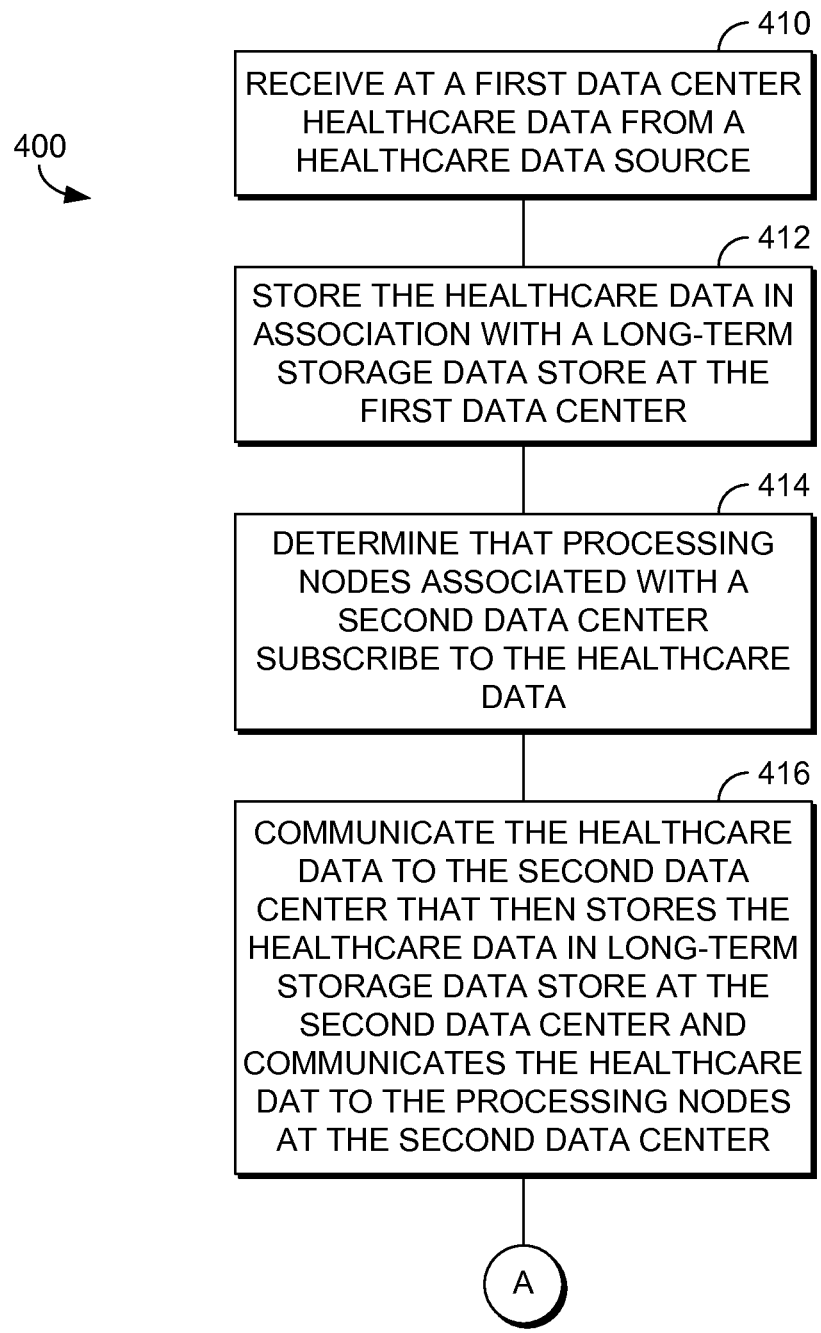

FIG. 4 depicts a flow diagram of an exemplary method 400 of synchronizing healthcare data across multiple data centers. As with the method 300, the term "step" is not meant to imply a specific order of operations. At a step 410, a piece of healthcare data is received at a first data center from a healthcare data source such as the healthcare data source 210 of FIG. 2. At a step 412, the piece of healthcare data is stored in association with a long-term storage data store located at the first data center. This holds true even if processing nodes associated with the first data center do not subscribe to the piece of healthcare data.

At a step 414, it is determined that one or more processing nodes associated with a second geographically-disparate data center subscribe to the piece of healthcare data. At a step 416, the piece of healthcare data is communicated to the second data center. The second data center subsequently stores the piece of healthcare data in association with its long-term storage data store; it also communicates the piece of healthcare data to the processing nodes that subscribe to the data. The steps 412 and 414 may be carried out substantially concurrently with each other.

As mentioned, the methods and systems outlined above are not limited to just two data centers. For example, it may be determined that one or more processing nodes associated with a third geographically-disparate processing node subscribe to the piece of healthcare data. The first data center communicates the piece of healthcare data to the third data center. The piece of healthcare data may be retrieved from the staging platform associated with the first data center. If, however, the piece of healthcare data has already been eliminated or deleted from the staging platform, it may be accessed from, for example, the long-term storage data store associated with the first or second data center and communicated to the third data center. Any and all such aspects, and any variation thereof, are contemplated as being within the scope of the invention.

Figure 5:
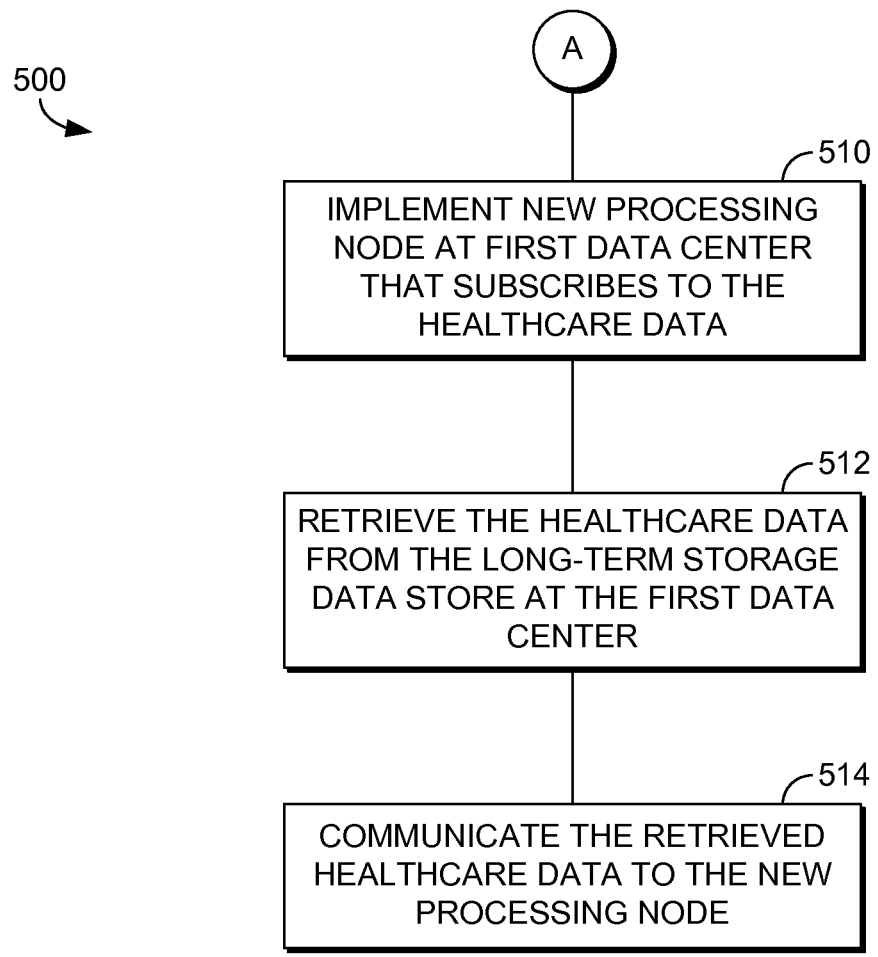

Turning to FIG. 5 which is a continuation of the method 400, at a step 510 the first data center implements a new computing solution on a processing node(s) that subscribes to the piece of healthcare data provided by the healthcare data source. At a step 512, the piece of healthcare data is retrieved from the long-term storage data store associated with the first data center. And, at a step 514, the piece of healthcare data is communicated to the processing node(s) executing the new computing solution. This eliminates the need to have to re-upload the piece of healthcare data from the healthcare data source.

As seen, the synchronization service described in this disclosure provides full disaster recovery capabilities by storing healthcare data received from a source at long-term storage data stores associated with two geographically-disparate data centers. As well, the synchronization service ensures that a healthcare data source need only upload data a single time to the service. The data is thereafter available to processing nodes across multiple disparate data centers. In addition, it is available to later-implemented solutions. This reduces the amount of processing resources expended by the healthcare data source and further keeps data center hosting costs down.

The present invention has been described in relation to particular embodiments, which are intended in all respects to be illustrative rather than restrictive. Further, the present invention is not limited to these embodiments, but variations and modifications may be made without departing from the scope of the present invention.

What is claimed is:

1. A computer-implemented system for synchronizing healthcare data across geographically-disparate data centers, the computer-implemented system including a server comprising:

a data collector service in a cloud computing platform communicating over a computer network utilizing at least one of a wired media, a wireless media, or a combination thereof and operable to:

receive healthcare data by communicating over the computer network from a plurality of healthcare data sources substantially simultaneously with the healthcare data being updated at the plurality of healthcare data source, and communicate the healthcare data to a first staging platform associated with a first data center, wherein the first data center is remote from the plurality of health care data sources, wherein the healthcare data is kept separate based on the healthcare data source from which it is received;

the first staging platform associated with the first data center operable to concurrently:

store the healthcare data in association with a first long-term storage data store located at the first data center, wherein the healthcare data is indexed so that it is optimized for low-latency processing and categorized based on the healthcare data source from which it was received;

communicate the healthcare data to one or more processing nodes associated with the first data center that subscribe to received healthcare data based on nature of a computing solution implemented by the one or more processing node associated with the first data center on the healthcare data to generate clinically-relevant data, wherein the healthcare data is communicated in real-time to each of the one or more processing node performing low-latency processing on the healthcare data; and communicate the healthcare data to a second staging platform associated with a second geographically-disparate data center, the second staging platform operable to store the healthcare data in association with a second long-term storage data store located at the second data center and communicate the healthcare data to one or more processing nodes associated with the second data center based on nature of the computing solution implemented by the one or more processing node associated with the second data center on the healthcare data to generate clinically-relevant data, wherein the healthcare data is communicated in real-time to each of the one or more processing node performing low-latency processing on the healthcare data, wherein the clinically-relevant data is provided through the computer network to one or more user computers via one or more computer applications.

2. The computer-implemented system of claim 1, wherein at least a portion of the plurality of healthcare data sources maintain disparate electronic medical record systems.

3. The computer-implemented system of claim 1, wherein the data collector service is referenced by a uniform resource locator (URL).

4. The computer-implemented system of claim 1, wherein the healthcare data is cleared from the first staging platform subsequent to the healthcare data: 1) being stored in association with the first long-term storage data store, 2) being communicated to the one or more processing nodes associated with the first data center, and 3) being communicated to the second staging platform.

5. The computer-implemented system of claim 1, wherein the data collector service is further operable to communicate an acknowledgement message to each of the plurality of healthcare data sources once the healthcare data has been communicated to the first staging platform associated with the first data center, the acknowledgment message acknowledging the receipt of the healthcare data.

6. The computer-implemented system of claim 1, wherein the first and second long-term storage data stores persistently store the healthcare data.

7. The computer-implemented system of claim 1, wherein at least one of the one or more processing nodes associated with the first data center is operable to perform batch processing on the healthcare data.

8. The computer-implemented system of claim 1, wherein at least one of the one or more processing nodes associated with the first data center is operable to perform low-latency processing on the healthcare data.

9. The computer-implemented system of claim 1, wherein at least one of the one or more processing nodes associated with the second data center is operable to perform batch processing on the healthcare data.

10. The computer-implemented system of claim 1, wherein at least one of the one or more processing nodes associated with the second data center is operable to perform low-latency processing on the healthcare data.

11. A computerized method carried out by at least one server having at least one processor for synchronizing healthcare data across data centers, the method comprising:

at a first data center concurrently:

receiving a set of healthcare data over a computer network from a healthcare data source substantially simultaneously with the healthcare data being updated at the plurality of healthcare data source, wherein the healthcare data is kept separate base on the healthcare data source from which it is received;

storing the set of healthcare data in association with a first long-term storage data store associated with the first data center, wherein the first data center is remote from the healthcare data source, wherein the healthcare data is indexed so that it is optimized for low-latency processing and categorized based on the healthcare data source from which it was received;

determining, using the at least one processor, one or more processing nodes associated with the first data center that subscribe to the set of healthcare data;

communicating the set of healthcare data to the one or more processing nodes associated with the first data center based on nature of a computing solution implemented by the one or more processing node associated with the first data center on the healthcare data to generate clinically-relevant data, wherein the healthcare data is communicated in real-time to each of the one or more processing node performing low-latency processing on the healthcare data;

determining that one or more processing nodes associated with a second data center subscribe to the set of healthcare data; and communicating the set of healthcare data to the second data center, wherein upon receipt of the set of healthcare data, the second data center stores the set of healthcare data in association with a second long-term storage data store associated with the second data center and communicates the set of healthcare data to the one more processing nodes associated with the second data center that subscribe to the set of healthcare data based on nature of the computing solution implemented by the one or more processing node associated with the second data center on the healthcare data to generate clinically-relevant data, wherein the healthcare data is communicated in real-time to each of the one or more processing node performing low-latency processing on the healthcare data, wherein the clinically-relevant data is provided through the computer network to one or more user computers via one or more computer applications.

12. The computerized method of claim 11, wherein the first data center is in a geographic location that is disparate from the second data center's geographic location.

13. The computerized method of claim 11, wherein the healthcare data source comprises a healthcare organization.

14. The computerized method of claim 11, further comprising:
receiving an updated set of healthcare data from the healthcare data source; and
storing the updated set of healthcare data as a new version of the set of healthcare data in association with the first long-term storage data store associated with the first data center.

15. The computerized method of claim 11, wherein the set of healthcare data is received only once from the healthcare data source.

16. The computerized method of claim 11, further comprising:
implementing a new processing node(s) at the first data center, the new processing node(s) subscribing to the set of healthcare data;
retrieving the set of healthcare data from the first long-term storage data store; and
communicating the retrieved set of healthcare data to the new processing node(s).

17. One or more computer-storage media having computer-executable instructions embodied thereon that, when executed, perform a method of synchronizing healthcare data across geographically-disparate data centers, the method comprising:
at a first data center concurrently:
receiving a piece of healthcare data over a computer network from a healthcare data source substantially simultaneously with the healthcare data being updated at the plurality of healthcare data source, wherein the healthcare data is kept separate based on the healthcare data source from which it is received;
storing the piece of healthcare data in association with a first long-term storage data store located at the first data center, wherein the first data center is remote from the healthcare data source, wherein the healthcare data is indexed so that it is optimized for low-latency processing and categorized based on the healthcare data source from which it was received;
determining that one or more processing nodes associated with a second geographically-disparate data center subscribe to the piece of healthcare data; and
communicating the piece of healthcare data to the second data center, the second data center storing the piece of healthcare data in association with a second long-term storage data store located at the second data center and communicating the piece of healthcare data to the one or more processing nodes that subscribe to the piece of healthcare data based on nature of a computing solution implemented by the one or more processing node associated with the second data center on the healthcare data to generate clinically-relevant data, wherein the healthcare data is communicated in real-time to each of the one or more processing node performing low-latency processing on the healthcare data,
wherein the clinically-relevant data is provided through the computer network to one or more user computers via one or more computer applications.

18. The media of claim 17, further comprising:
determining that one or more processing nodes associated with a third geographically-disparate data center subscribe to the piece of healthcare data; and
communicating the piece of healthcare data to the third data center, the third data center storing the piece of healthcare data in association with a third long-term storage data store located at the third data center and communicating the piece of healthcare data to the one or more processing nodes associated with the third data center that subscribe to the piece of healthcare data.

19. The media of claim 17, further comprising:
determining that one or more processing nodes associated with the first data center subscribe to the piece of healthcare data; and
communicating the piece of healthcare data to the one or more processing nodes associated with the first data center.

20. The media of claim 17, wherein the first data center communicates the piece of healthcare data to the second data center substantially simultaneously with when the piece of healthcare data was received by the first data center.

* * * * *